US012735551B2

(12) United States Patent
Fragiacomo et al.

(10) Patent No.: US 12,735,551 B2
(45) Date of Patent: Sep. 15, 2026

(54) PROCESS FOR PRODUCING BIS(2-HYDROXYETHYL) TEREPHTHALATE IN LIQUID FORM BY DEPOLYMERIZATION OF POLYETHYLENE TEREPHTHALATE (PET)

(71) Applicant: Chempet S.r.l., Cerano (IT)

(72) Inventors: Guido Fragiacomo, Novara (IT); Gabriele Nipoti, Tromello (IT); Gianluigi Noja, Novara (IT)

(73) Assignee: Chempet S.r.I, Cerano (IT)

( * ) Notice: Subject to any disclaimer, the term of this patent is extended or adjusted under 35 U.S.C. 154(b) by 545 days.

(21) Appl. No.: 18/276,303

(22) PCT Filed: Feb. 24, 2022

(86) PCT No.: PCT/IB2022/051632

§ 371 (c)(1),
(2) Date: Aug. 8, 2023

(87) PCT Pub. No.: WO2022/180563

PCT Pub. Date: Sep. 1, 2022

(65) Prior Publication Data

US 2024/0110033 A1 Apr. 4, 2024

(30) Foreign Application Priority Data

Feb. 24, 2021 (IT) ........................ 102021000004286

(51) Int. Cl.
*C08J 11/24* (2006.01)
*C07C 67/08* (2006.01)
*C07C 67/52* (2006.01)
*C08G 63/183* (2006.01)
*C08G 63/80* (2006.01)

(52) U.S. Cl.
CPC ............... *C08J 11/24* (2013.01); *C07C 67/08* (2013.01); *C07C 67/52* (2013.01); *C08G 63/183* (2013.01); *C08G 63/80* (2013.01); *C08J 2367/03* (2013.01)

(58) Field of Classification Search
CPC ........ C08G 63/183; C08G 63/80; C08J 11/24; C08J 2367/03; C08J 2367/02; C07C 67/52; C07C 67/08; C07C 67/03; C07C 69/82; Y02W 30/62
See application file for complete search history.

(56) References Cited

U.S. PATENT DOCUMENTS

| | | | |
|---|---|---|---|
| 3,222,299 A | 12/1965 | MacDowell | |
| 3,668,235 A | 6/1972 | Ichikawa et al. | |
| 4,609,680 A | 9/1986 | Fujita et al. | |
| 6,630,601 B1 | 10/2003 | Inada et al. | |
| 7,030,264 B1 * | 4/2006 | Inada | C08J 11/24 560/96 |
| 7,087,706 B2 † | 8/2006 | Caldwell | |
| 2004/0182782 A1 | 9/2004 | Inada et al. | |
| 2015/0246312 A1 | 9/2015 | Dube et al. | |
| 2020/0190280 A1 | 6/2020 | Lin et al. | |

FOREIGN PATENT DOCUMENTS

| | | | |
|---|---|---|---|
| EP | 0723951 A1 † | 1/1996 |
| EP | 1672000 A1 † | 6/2006 |
| EP | 1234812 B1 | 5/2008 |
| JP | 4637577 A | 11/1971 |
| JP | 2003055300 A | 2/2003 |
| JP | 2003-305358 A † | 10/2003 |
| JP | 2004231855 A | 8/2004 |
| JP | 2005330444 A | 12/2005 |
| JP | 2006232701 A | 9/2006 |
| JP | 2008-088096 † | 4/2008 |
| JP | 2008088096 A | 4/2008 |
| WO | WO-2005035621 A1 | 4/2005 |
| WO | WO-2021028695 A1 | 2/2021 |
| WO | WO-2021124149 A1 | 6/2021 |

OTHER PUBLICATIONS

Kodaira, Y., Saito, S., Kobayashi, H., "Esterification Reaction with Ethylene Glycol of Terephthalic Acid in the Presence of Bis(2-Hydroxyethyl) Terephthalate or lower Polymer Thereof", Journal of Industrial Chemistry, 1971, vol. 74, No. 11, pp. 2387-2392 (with English abstract).

(Continued)

*Primary Examiner* — Monica A Huson
(74) *Attorney, Agent, or Firm* — Element IP, PLC

(57) ABSTRACT

Described in a process for producing bis(2-hydroxyethyl) terephthalate (BHET) in liquid form by depolymerization of polyethylene terephthalate (PET), wherein BHET obtained from depolymerization by glycolysis with monoethylene glycol (MEG) is purified and subsequently crystallized by cooling to obtain BHET in crystalline form impregnated with a solvent. The BHET is then melted down to obtain a solution of BHET in the solvent. The solvent content in the resulting BHET solution is adjusted, if necessary, to a value such that the BHET is in a liquid form at a temperature of less than or equal to 90° C. and greater than or equal to 70° C. This provides a BHET in liquid form that is stable for a long time within the above temperature range, which can be stored, transported, and fed to the polycondensation reactor for PET production.

10 Claims, No Drawings

(56) References Cited

OTHER PUBLICATIONS

Kiriyama, G., “Change in State of Binary System”, Niigata Prefectural Education Center Research Report, 1977, No. 16, pp. 27-32 (with English abstract).
International Search Report and Written Opinion issued Jun. 29, 2022 in PCT/IB2022/051632, 10 pages.
Official Action issued on Jan. 8, 2026, in corresponding Indonesian Patent Application No. P00202307687 (with English translation), 6 pages.
ASTM D7409-15, “Standard Test Method for Carboxyl End Group Content of Polyethylene Terephthalate (PET) YarnsI”, 2020, ASTM International, 3 pages.
ASTM D1613-17, “Standard Test Method for Acidity in Volatile Solvents and Chemical Intermediates Used in Paint, Varnish, Lacquer, and Related Products”, ASTM International, Retrieved from: https://www.doc88.com/n-90199866219112.html, 2023, 3 pages.
Office Action issued Sep. 2, 2025, in corresponding Japanese Patent Application No. 2023-550057 (with English translation), 18 pages.

* cited by examiner
† cited by third party

PROCESS FOR PRODUCING BIS(2-HYDROXYETHYL) TEREPHTHALATE IN LIQUID FORM BY DEPOLYMERIZATION OF POLYETHYLENE TEREPHTHALATE (PET)

The present invention relates to a process for producing bis(2-hydroxyethyl) terephthalate in liquid form by depolymerization of polyethylene terephthalate (PET), in particular PET from post-industrial and post-consumer waste.

Polyethylene terephthalate (PET) is a widely used semi-crystalline thermoplastic polyester with high strength and transparency, which has several applications thanks to its physical and chemical properties, in particular in packaging and fibre production. Global PET production reached a capacity of more than 70 million tonnes (Mton) in 2017, of which around 15 Mton was produced in Europe, for manufacturing synthetic fibres (around 67%), bottles (around 23%) and packaging (10%).

PET poses no safety risk, but increased consumption and accumulation in waste streams and its non-biodegradability raise environmental and economic concerns. Therefore, there is a growing interest in PET recycling technologies.

PET is considered to be a polymeric material that can be easily recycled and its recycling is the most common among polymeric materials. The technologies can be grouped into two macro-categories: mechanical and chemical recycling.

Mechanical recycling consists mainly in obtaining PET flakes, by crushing and grinding previously sorted waste, which are sent directly to extrusion to produce new articles. The main problems with this technology are due to heterogeneity of solid waste and to low quality of the final product, as PET deteriorates its mechanical properties with each recycling process.

Nevertheless, to date mechanical recycling is still the most widely used technology for the treatment of waste containing PET, although it does not produce a high quality material suitable for food contact. There is therefore a growing interest in chemical recycling technologies as they comply with the principles of sustainable development, returning raw materials for the production of virgin PET, which is of course of much higher quality than mechanically recycled PET.

Chemical recycling involves decomposing the polyester using a reagent capable of depolymerizing the PET chains to obtain the starting monomers; chemical depolymerization of PET is usually obtained by hydrolysis or methanolysis or glycolysis.

Hydrolysis depolymerizes PET into terephthalic acid (TPA) and monoethylene glycol (MEG) (also called ethylene glycol—EG) by reaction with water. Methanolysis degrades PET to dimethyl terephthalate (DMT) and MEG by reaction with methanol. Glycolysis causes the depolymerization by reaction with MEG to produce bis(2-hydroxyethyl) terephthalate (BHET), an intermediate product formed in the first stage of PET production from the starting monomers (terephthalic acid and MEG).

At the end of the glycolysis reaction, BHET is obtained in the form of a solution in water or MEG or mixtures thereof. The BHET is then crystallised, filtered, purified and partially dried. BHET obtained from the depolymerization of recycled PET is often referred to as 'r-BHET'.

This produces a BHET in crystalline form that still contains a significant amount of residual solvent, typically around 20%-40% by weight (this wet product is often referred to as "cake"). Although this amount of liquid can be reduced by controlling the size of the BHET crystals, the "cake" must necessarily be subjected to anhydrification and flaking in order to obtain dry BHET in flake form.

In order to facilitate drying, it is necessary to carry out thorough washing with water in order to remove MEG, whose boiling point is much higher than that of water and would therefore require higher temperatures and/or much longer times, making drying even slower and more energy-consuming, as well as increasing the quantity of oligomers.

Thus, r-BHET can be fed to polycondensation rectors for the production of virgin PET as an additional raw material to the more commonly used monomers, i.e. TPA and MEG, or, in some cases, r-BHET can be the main or even exclusive monomer for the production of new PET.

Drying can be achieved by known industrial processes, in particular by evaporation of the solvent, which is mostly water. However, especially if the plant is designed for large-scale production of r-BHET (e.g. hundreds of tonnes/day), the drying phase requires the use of a large dryer, which consumes a lot of energy to keep the product at a temperature that allows the solvent to evaporate as quickly as possible, but also prevents the BHET from melting in the mixture with the solvent. In fact, even partial melting would make product handling difficult, hindering the solvent evaporation process and plant operation. Therefore, the drying temperature is generally maintained at around 40°-60° C., so evaporation is very slow. In addition, maintaining BHET for very long periods at relatively high temperatures leads to a deterioration in the characteristics of the product, which tends to form degradation by-products.

In addition, the production of BHET flakes can cause the formation of fine dust, which requires appropriate safety measures to be taken, as BHET fine dust is weakly explosive and in any case flammable, so the plant must be constructed to be explosion-proof (e.g. according to European Atex standards).

After drying, r-BHET is usually packed in "big bags" ranging in size from 20 kg to 2 tonnes each, made of a polypropylene fabric with a polyethylene lining to ensure high mechanical strength and impermeability to moisture.

The end-user of r-BHET in a PET plant producing PET by polycondensation of terephthalic acid (which is in the form of solid flakes) and ethylene glycol, needs to have ad hoc equipment for the storage and pneumatic transport of r-BHET, which considerably increases the cost and complexity of the plant itself, especially when working with large product volumes (in the order of tonnes). Storing r-BHET in large silos considerably increases the risk of packing due to compression of the material and moisture penetration, with formation of agglomerates. This worsens the characteristics of the product in particular with regard to flowability, leading to problems during use in the PET production plant.

U.S. Pat. No. 3,668,235 describes a process for removing a volatile liquid from a solid BHET which is soaked by said liquid, which involves heating the product to a molten mass, from which the liquid is removed by evaporation. This results in a solid BHET with a significant reduction in material heating time.

More specifically, the liquid-impregnated BHET (cake) is fed into a melter where it is melted at a temperature typically between 120° C. and 140° C. The melt is then fed into a high-efficiency evaporator, such as a thin-film or flash evaporator. This results in a BHET with a liquid content of around 10%-15% by weight. To obtain BHET flakes, it is then sent to a desiccator, where a temperature of around 130° C. is maintained until the liquid content is reduced to less than 1% by weight. The anhydrified BHET is then reduced to flakes, typically 1 mm to 10 mm in size.

The Applicant therefore has posed the technical problem of having r-BHET in liquid form that could be stored, transported and fed to the polycondensation reactor for the production of PET, thus avoiding reducing r-BHET to flakes by drying, a process which, as indicated above, involves numerous plant engineering problems and high energy consumption, and requires the adoption of particularly stringent safety standards.

The Applicant has found that BHET, which is obtained after depolymerization of PET and subsequent purification and crystallization, is presented as a solid impregnated by a solvent, which is generally water and/or MEG, the melting temperature of which depends significantly on the solvent content. In fact, the presence of a solvent reduces the melting temperature of BHET and therefore allows the product to be melted at significantly lower temperatures with respect to essentially solvent-free BHET. This allows BHET to be obtained in liquid form at a temperature less than or equal to 90° C., in particular from 70° C. to 90° C. These are temperatures at which BHET is in liquid form, with no suspended solids, and is stable even over long storage periods. At these temperatures, the tendency of BHET to form oligomers is very low, resulting in a product with stable characteristics suitable for use in a polycondensation process to produce PET. Therefore, BHET can be transported and stored in liquid form at a temperature less than or equal to 90° C., i.e. at a temperature that does not require the adoption of special safety measures, such as ADR regulations for the transport of dangerous products.

According to a first aspect, the present invention therefore relates to a process for producing bis(2-hydroxyethyl) terephthalate in liquid form by depolymerization of polyethylene terephthalate (PET), comprising:

(a) depolymerizing a PET by glycolysis with monoethylene glycol (MEG), to obtain a crude BHET solution;
(b) subjecting the crude BHET solution to purification to obtain a purified BHET solution;
(c) subjecting the purified BHET solution to crystallization by cooling, so as to obtain BHET in crystalline form impregnated with a solvent;
(d) preparing, by melting the BHET in crystalline form obtained from step (c), a solution of BHET in the solvent at a temperature lower than or equal to 90° C. and higher than or equal to 70° C., possibly adjusting, if necessary, the solvent content in the BHET solution thus obtained to a value such as to obtain a melting temperature of the BHET within the limits indicated above.

The resulting liquid BHET can be transported and stored for a long time at a temperature greater than or equal to 70° C. and less than or equal to 90° C. Under these conditions, the product is stable and meets the quality standards required for r-BHET to be used in a polycondensation process for producing PET. The amount of solvent mixed with BHET, which is usually constituted by water and/or MEG, is in fact fully compatible with polycondensation processes, which are designed to handle a certain amount of water, formed by the esterification reaction, which substantially corresponds to the amount of water that is present in the BHET in liquid form obtained by the process according to the present invention and which allows to melt and maintain the product in liquid form at a temperature less than or equal to 90° C. On the other hand, MEG is the comonomer used together with TPA for the production of PET, which is usually fed in excess with respect to the stoichiometric quantity, so that the introduction of other MEG together with BHET generally does not represent a problem for the polycondensation reaction, which can be adjusted if necessary in order to take into account the contribution of MEG deriving from the feeding of BHET in liquid form.

The Applicant has determined that, if the solvent is water, the amount of water such as to obtain a melting temperature of the BHET crystals impregnated with water from 70° C. to 90° C. is variable from 12% to 20% by weight (with respect to the total weight of the mixture between BHET and solvent). This amount of water essentially corresponds to the amount of water that would be obtained as a result of the esterification reaction between an equivalent amount of terephthalic acid and MEG. This is therefore a quantity of water compatible with the polycondensation process for PET production.

If the solvent is MEG, the amount of MEG to be used to achieve a melting temperature from 70° C. to 90° C. is significantly higher than that required in the case of water. The Applicant has determined that this amount varies from 25% to 40% by weight (with respect to the total weight of the mixture of BHET and solvent).

In the case of water+MEG mixtures, the amount of solvent shall be intermediate between the two ranges above and will depend on the ratio of water to MEG. For example, for a weight ratio of water to MEG from 0.5 to 2, the amount of water solvent+MEG to be used to achieve a melting temperature from 70° C. to 90° C. is from 15% to 30% by weight (relative to the total weight of the mixture of BHET and solvent).

In a second aspect, the present invention relates to a process for producing polyethylene terephthalate (PET) which comprises:

producing bis(2-hydroxyethyl) terephthalate (BHET) in liquid form by depolymerization of recycled polyethylene terephthalate (PET) according to the process described above;

using said BHET as the main monomer for the production of PET by polycondensation, or as a secondary monomer in a polycondensation process of terephthalic acid (TPA) and monoethylene glycol (MEG).

It is important to note that BHET in liquid form obtained according to the present invention has a significantly higher amount of free carboxyl groups and acid number than dried BHET. Higher acidity of BHET is an advantage from the point of view of PET production, as it increases the reactivity of BHET and thus the polycondensation rate.

Preferably, the BHET in liquid form according to the present invention has an amount of free carboxyl groups (CEG), measured according to ASTM D7409-15, from 40 to 100 mmol/kg, more preferably from 60 to 80 mmol/kg.

Preferably the BHET in liquid form according to the present invention has an acid number, measured according to ASTM D1613-17, from 2 to 6 mg KOH/g, more preferably 3 to 5 mg KOH/g.

As regards step (a) of depolymerization of PET by glycolysis with monoethylene glycol (MEG), this is preferably carried out with a recycled PET, i.e. obtained by recovery from post-consumer and/or post-industrial waste. Such waste can come from a wide variety of applications such as:

transparent and/or coloured PET bottles for water, soft drinks, carbonated beverages, and the like;

opaque PET articles, where the PET contains fillers such as titanium oxide, carbon black, silicates and other pigments;

multilayer PET articles, typically for the food industry, in which the PET layers are coupled with layers of gas barrier polymers (e.g. nylon, polyvinyl alcohol (EVOH), polyvinyl acetate (EVA)) or metal sheets (e.g. aluminium sheets) or polyolefin sheets;

printed PET sheets;

PET fibres, fabrics and non-woven fabrics.

The glycolysis reaction is usually carried out in the presence of a heterogeneous transesterification catalyst. The catalyst may be selected, for example, from: Na, Mg, Zn, Cd, Mn, Co, Ca or Ba carbonates, fatty acid salts or borates (e.g., zinc borate, zinc acetate, sodium carbonate).

Preferably, the glycolysis reaction is carried out at a temperature of from 170° C. to 270° C., more preferably from 195° C. to 210° C.

In the glycolysis reaction, MEG is generally used in quantities of from 1.0 to 10.0 parts by weight, preferably from 1.5 to 6.0 parts by weight, depending on the parts by weight of PET waste.

The duration of the glycolysis reaction can vary within wide ranges, depending on the reaction conditions, such as temperature, agitation, type of reactor and the like. Usually the reaction time is from 0.2 hours to 8 hours, preferably from 0.5 hours to 3 hours. The reaction can be carried out in batch or continuously. The reaction pressure is usually atmospheric pressure, but a reduced or increased pressure may be used.

Further details concerning the glycolysis reaction of a PET waste to recover BHET are provided, for example, in U.S. Pat. Nos. 3,222,299, 4,609,680 and EP 0 723 951 A1.

The product obtained from the glycolysis reaction is a crude BHET solution, in which BHET is dissolved in MEG along with various contaminants that result from the specific composition of the PET waste. Typically, the crude BHET solution also contains BHET oligomers, preferably dimers and/or trimers. In this description and the appended claims, BHET means not only BHET as such (monomer), but also its oligomers.

Contaminants are ingredients of the PET waste or derivatives obtained by glycolysis of such ingredients, such as:

dyes, usually organic dyes;

inks;

adhesives and glues;

polyolefins, e.g. polyethylene or polypropylene used to produce caps;

PET-G;

biodegradable polymers, e.g. PLA;

gas barrier polymers, e.g. polyamides, polyvinyl alcohol (EVOH), polyvinyl acetate (EVA);

UV absorbers;

fillers, e.g. titanium dioxide, carbon black, silica, silicates and other pigments;

metal sheets and fragments thereof, e.g. aluminium sheets.

The crude BHET solution can be subjected to step (b) of purification according to known methods. In particular, the raw glycolized product may be subjected to filtration to separate insoluble contaminants, and possibly to treatment to remove soluble contaminants, for example by an adsorbent agent or by oxidation and subsequent treatment with an adsorbent agent.

In order to reduce the solubility of certain contaminants in the crude BHET solution, such as polyamides, glues and the like, water is preferably added to the crude BHET solution to allow precipitation of such insoluble contaminants, but keeping the BHET and oligomers thereof in solution. Insoluble contaminants are then separated from the crude BHET solution, usually by filtration. In the resulting crude BHET solution after filtration, BHET and oligomers thereof are therefore dissolved in a mixture of water and MEG.

Further details of the purification step (b) can be found for example in US 2004/0182782, EP 1 234 812, U.S. Pat. No. 6,630,601, and also in international patent application PCT/IB2020/062026, in the name of the same Applicant.

After the purification step (b), the purified BHET solution is subjected to crystallization by cooling (step (c)). This produces BHET in crystalline form impregnated by the solvent, i.e. with the crystallization mother liquors. This product takes the form of a solid mixed intimately with the liquid phase, which is referred to in jargon as "cake". The amount of solvent is usually comprised between 15% and 50% by weight, preferably between 20% and 40% by weight, relative to the total weight of BHET and solvent.

The solvent-impregnated BHET in crystalline form is then melted (step (d)) by heating to a temperature above the melting temperature of the solvent-impregnated BHET. Based on the experiments carried out by the Applicant, this melting temperature depends mainly on the nature of the solvent and its quantity. In this respect, see the data in Example 1 below.

In practice, based on the characteristics of the product generally obtained from the crystallization step (c), the melting step (d) can be conducted by heating the BHET to a temperature comprised between 70° C. and 95° C., preferably between 80° C. and 85° C.

If the solvent content in the BHET obtained from the melting step (d) is not suitable for obtaining a solution of BHET in the solvent at a temperature less than or equal to 90° C. and greater than or equal to 70° C., the solvent content may be adjusted according to known techniques. As the solvent content is usually too high compared to what is required, this can be partially reduced by evaporation. This can be achieved, for example, by means of a high-efficiency evaporator, such as a thin-film evaporator or a flash evaporator. In the less frequent case where the amount of solvent is too low, it is possible to add solvent until the desired result is obtained, i.e. the BHET is in liquid form at a temperature less than or equal to 90° C. and greater than or equal to 70° C.

It should be noted that in the event that it is necessary to reduce the amount of solvent, for example by evaporation, the adjustment step is generally quick, much faster than a step of complete drying of the BHET as required by the known art, since the amount of solvent to be removed is very small, and does not require special precautions to prevent degradation or excessive oligomerization of the BHET.

The solvent content adjustment step, if any, can be carried out in the BHET production plant or, alternatively, can be carried out at the inlet of the polycondensation plant for PET production, so as to adjust the solvent quantity according to the specifications required by the polycondensation plant.

BHET in liquid form thus obtained can be stored for long periods at a temperature less than or equal to 90° C. and transported at this temperature without special safety precautions. For storage and transport, stainless steel containers can be used, for example, in accordance with ISO standards, which are suitable for transporting liquids at controlled temperatures. The headspace of the containers may contain air or, preferably, an inert gas (e.g. nitrogen).

The following examples are provided purely for the purpose of illustrating the present invention and should not be regarded as limiting the scope of protection defined by the appended claims.

EXAMPLE 1

The melting (Tm) and crystallization (Tc) temperatures of a BHET impregnated with different solvents, i.e. water, MEG and water/MEG mixtures, were measured.

BHET was obtained by glycolysis of recycled PET and purification. The characteristics of the dried BHET were as follows:

residual water: 0.13% by weight of the total;
residual metals: 1.39 ppm;
BHET 96.8% by weight;
BHET dimer 2.82% by weight;
BHET trimer<0.1% by weight;
BHET was also assessed by spectrophotometric analysis to determine the amount of residues after purification. For this purpose, a sample of BHET flakes was dissolved in DMSO (weight ratio 1:1) and the solution was introduced into a spectrophotometer to record the UV-VIS spectrum. Table 1 shows the absorbance values at predefined wavelengths and the overall absorbance value at these wavelengths (Σabs):

TABLE 1

| Wavelength (nm) | Absorbance |
|---|---|
| 475 | 0.016 |
| 510 | 0.016 |
| 570 | 0.014 |
| 590 | 0.009 |
| 650 | 0.008 |
| | Σabs = 0.055 |

The colour of the BHET flakes was determined using Hunter Lab Colour Scale according to Hunter Lab Colour Space L, a, b (details of this measurement can be found on the website https://support.hunterlab.com). The measurement was carried out on a cylindrical sample (diameter: 50 mm; height: 10 mm) of dry BHET obtained by compressing the flakes in a cylindrical container at 400 bar. These are the measured parameters L, a, b: L=98.37, a=0.05, b=0.95.

The BHET crystals were mixed with different solvents (water, MEG or mixtures thereof) in different amounts. The melting (Tm) and crystallization (Tc) temperatures were then measured. The results are shown in Table 2 (percentages are by weight in relation to the total weight of BHET+ solvent).

TABLE 2

| | Product | % BHET | $H_2O$ | % MEG | Tm (° C.) | Tc (° C.) |
|---|---|---|---|---|---|---|
| BHET | 1 | 100 | — | — | 115 | — |
| BHET + $H_2O$ | 2 | 90.0 | 10.0 | — | 91.8 | 80.0 |
| | 3 | 87.6 | 12.4 | — | 84.8 | 67.0 |
| | 4 | 85.0 | 15.0 | — | 80.0 | 63.0 |
| | 5 | 80.0 | 20.0 | — | 70.3 | 54.0 |
| BHET + MEG | 6 | 90.0 | — | 10.0 | 99.5 | 83.5 |
| | 7 | 87.6 | — | 12.4 | 98.6 | 82.5 |
| | 8 | 85.0 | — | 15.0 | 94.6 | 75.7 |
| | 9 | 80.0 | — | 20.0 | 90.7 | 72.0 |
| BHET + | 10 | 87.6 | 4.3 | 8.1 | 92.0 | 77.0 |
| $H_2O$ + MEG | 11 | 87.6 | 6.2 | 6.2 | 88.2 | 72.0 |
| | 12 | 87.6 | 8.1 | 4.3 | 88.2 | 68.0 |

In the case of MEG alone as a solvent, the above data made it possible to draw a calibration curve for Tm variation of a function of MEG amount, from which the following values were calculated:

TABLE 3

| | % BHET | % MEG | Tm (° C.) |
|---|---|---|---|
| BHET + MEG | 70.0 | 30.0 | 82.0 |
| | 67.6 | 33.0 | 79.0 |
| | 60.0 | 40.0 | 73.0 |

The following can be seen from the data in Table 2 and 3.

Pure BHET could only be stored and transported in liquid form at a temperature higher than 115° C. This is a too high temperature, which would lead to problems of product stability and complex safety measures (according to ADR regulations).

Note that the melting temperature of pure BHET (CAS Number: 959-26-2) is 106-109° C. However, based on the Applicant's experience, it is considered that in order to ensure that the product is in a stable liquid form, the temperature must be maintained at a value significantly higher than the charted melting temperature. Therefore, in practice, BHET must be maintained at a temperature above 115° C. to ensure that it is completely and stably in liquid form.

In the case of products containing only water as a solvent (products 2-5), it can be seen that a lowering of the melting temperature below 90° C. is achieved with amounts of water exceeding 10% by weight.

In products in which only MEG is used as a solvent (products 6-9), for quantities of MEG less than or equal to 20% by weight the melting temperature remains above 90° C.

For products in which an $H_2O$/MEG mixture was used (products 10-12), an $H_2O$/MEG ratio of around 1 or higher should be used to achieve a melting temperature below 90° C., at least with a total solvent quantity of 12.4% by weight (of the total).

EXAMPLE 2

The stability over time of different BHET compositions in liquid form, maintained under a nitrogen atmosphere, was evaluated compared to the starting BHET. The stability was assessed using three different parameters:

(i) change in BHET composition in terms of monomer, dimer and trimer, determined by HPLC analysis (% peak area);
(ii) change in the CEG (free carboxyl groups) content;
(iii) change in colorimetric characteristics, as determined in Example 1.

The starting BHET was obtained by glycolysis of recycled PET and subsequent purification. The characteristics of the dried BHET were as follows:

residual water: 0.20% by weight of the total;
residual metals: 1.39 ppm;
BHET 96.8% by weight;
BHET dimer 2.82% by weight;
BHET trimer<0.1% by weight;

Spectrophotometric Analysis:

TABLE 4

| Wavelength (nm) | Absorbance |
|---|---|
| 475 | 0.016 |
| 510 | 0.016 |
| 570 | 0.014 |

TABLE 4-continued

| Wavelength (nm) | Absorbance |
|---|---|
| 590 | 0.009 |
| 650 | 0.008 |
| | Σabs = 0.055 |

L=98.37, a=0.05, b=0.95.

(A) Stability test of dried BHET as such, kept in liquid state at 130° C. for 14 days (under nitrogen atmosphere).

Table 5 shows the stability parameters measured daily on the BHET sample:

TABLE 5

| Days | % monomer | % dimer | % trimer | % CEG | Σabs | L | a | b |
|---|---|---|---|---|---|---|---|---|
| 0 | 96.8 | 2.8 | 0.1 | <0.1 | 0.061 | 98.37 | 0.05 | 0.95 |
| 1 | 96.0 | 3.2 | 0.1 | 0.6 | — | — | — | — |
| 4 | 89.9 | 8.9 | 0.7 | 0.4 | — | — | — | — |
| 5 | 89.6 | 9.2 | 0.8 | 0.2 | — | — | — | — |
| 6 | 87.8 | 10.7 | 1.1 | 0.1 | — | — | — | — |
| 7 | 87.2 | 11.0 | 1.4 | 0.3 | — | — | — | — |
| 10 | 81.5 | 15.5 | 2.6 | 0.2 | — | — | — | — |
| 11 | 79.1 | 17.4 | 3.0 | 0.3 | — | — | — | — |
| 12 | 79.5 | 17.2 | 3.0 | 0.4 | — | — | — | — |
| 13 | 74.7 | 20.9 | 4.0 | 0.3 | — | — | — | — |
| 14 | 75.7 | 20.4 | 3.5 | 0.3 | 0.103 | 97.68 | 0.06 | 1.63 |

Spectrophotometric measurements were carried out only on the initial sample and on the final sample after 14 days of ageing. The yellowing of the sample as a result of ageing was also visible to the naked eye.

As can be seen from the data in Table 5, dried BHET kept in a liquid state at 130° C. (in an inert atmosphere) formed high amounts of oligomers, with a decrease in the amount of monomer of more than 20% after 14 days of ageing. The CEG content increased slightly, while a noticeable yellowing of the product was observed.

(B) Stability test of a solution of BHET in water (BHET=87.6 wt. %, $H_2O$=12.4 wt. %), kept in the liquid state at 80° C. for 14 days (under nitrogen atmosphere).

Table 6 shows the stability parameters measured daily on the BHET sample dissolved in water:

TABLE 6

| Days | % monomer | % dimer | % trimer | % CEG | Σabs | L | a | b |
|---|---|---|---|---|---|---|---|---|
| 0 | 96.8 | 2.8 | 0.1 | 0.1 | 0.061 | 98.37 | 0.05 | 0.95 |
| 1 | 97.8 | 1.9 | 0.1 | 0.3 | — | — | — | — |
| 2 | 97.6 | 2.0 | 0.1 | 0.4 | — | — | — | — |
| 3 | 97.3 | 2.1 | 0.1 | 0.5 | — | — | — | — |
| 4 | 96.4 | 2.5 | 0.1 | 0.8 | — | — | — | — |
| 7 | 96.3 | 2.4 | 0.1 | 1.0 | — | — | — | — |
| 8 | 96.2 | 2.2 | 0.1 | 1.5 | — | — | — | — |
| 9 | 96.2 | 2.2 | 0.1 | 1.3 | — | — | — | — |
| 10 | 95.5 | 2.6 | 0.1 | 1.7 | — | — | — | — |
| 13 | 94.8 | 2.9 | 0.1 | 2.1 | — | — | — | — |
| 14 | 94.9 | 2.7 | 0.1 | 2.1 | 0.028 | 99.01 | 0.01 | 0.83 |

Spectrophotometric measurements were carried out only on the initial sample and on the final sample after 14 days of ageing. After ageing, no yellowing was observed with the naked eye or by spectrophotometric analysis.

As can be seen from the data in Table 6, after ageing at 80° C. for 14 days (in a nitrogen atmosphere), the amount of BHET monomer decreased by only 2%, while the amounts of dimer and trimer did not change. The small decrease in the content of BHET monomer is attributable to the hydrolysis of the product, as shown by the increase in the CEG value.

Table 7 below compares the characteristics of the initial dried BHET and the BHET solution in water (BHET=87.6% by weight, $H_2O$=12.4% by weight) after 14 days of ageing at 80° C.

TABLE 7

| | % monomer | % dimer | % trimer | % CEG | CEG (mmol/kg) | number of acidities (mgKOH/g) |
|---|---|---|---|---|---|---|
| Dried BHET (as such) | 96.8 | 2.8 | 0.1 | 0.1 | 8.1 | 0.46 |
| BHET + $H_2O$ 12.4%, after 14 days at 80° C. | 94.9 | 2.7 | 0.1 | 2.1 | 75.7 | 4.25 |

It can be seen that after 14 days of ageing, the BHET solution remained stable, with no oligomer formation. A slight decrease in the BHET monomer content can be observed due to hydrolysis, which resulted in an increase in acidity. As indicated above, this is an advantage from the point of view of the polycondensation rate in the PET production reactor.

The invention claimed is:

1. A process for producing bis(2-hydroxyethyl) terephthalate (BHET) in liquid form by depolymerization of polyethylene terephthalate (PET), the process comprising:

(a) depolymerizing a PET by glycolysis with monoethylene glycol (MEG) to obtain a crude BHET solution;

(b) subjecting the crude BHET solution to purification to obtain a purified BHET solution;

(c) subjecting the purified BHET solution to crystallization by cooling to obtain BHET in crystalline form impregnated with a solvent; and (d) preparing, by melting the BHET in crystalline form, a solution of BHET in the solvent at a temperature lower than or equal to 90° C. and higher than or equal to 70° C. by optionally adjusting a content of the solvent in the BHET solution thus obtained to a value to obtain a melting temperature of the BHET within a range of from 70° C. to 90° C., wherein the solvent is water, and an amount of water is from 12% to 20% by weight with respect to a total weight of the solution of the BHET and water to obtain the melting temperature of the BHET of from 70° C. to 90° C.; or the solvent is a mixture of water and MEG in a water/MEG weight ratio of from 0.5 to 2, and an amount of the mixture of water and MEG is from 15% to 30% by weight with respect to a total weight of the solution of the BHET and the mixture to obtain the melting temperature of the BHET of from 70° C. to 90° C.

2. The process according to claim 1, wherein the BHET in liquid form obtained by the process contains free carboxylic groups (CEG), measured according to the ASTM D7409-15 standard, in an amount of from 40 to 100 mmol/kg.

3. The process according to claim 1, wherein the BHET in liquid form obtained by the process has an acid number, measured according to the ASTM D1613-17 standard, from 2 to 6 mgKOH/g.

4. The process according to claim 1, wherein the PET in the depolymerizing (a) is a recycled PET obtained by recovery from post-consumer and/or post-industrial waste.

5. The process according to claim 1, wherein the purification in (b) comprises filtration to separate insoluble contaminants, and optionally removal of soluble contaminants via an adsorbing agent or by oxidation and subsequent treatment with an adsorbing agent.

6. The process according to claim 1, wherein the BHET in crystalline form obtained after (c) is impregnated with an amount of the solvent from 15% to 50% by weight, with respect to a total weight of the BHET and the solvent.

7. The process according to claim 1, wherein the melting in (d) is carried out by heating the BHET at a temperature ranging from 80° C. to 85° C.

8. The process according to claim 1, wherein the content of the solvent is adjusted in (d) to remove excess solvent by evaporation of the solvent until the BHET is obtained in liquid form at a temperature lower than or equal to 90° C. and higher than or equal to 70° C.

9. The process according to claim 1, wherein the content of the solvent is adjusted in (d) by adding the solvent until BHET is obtained in liquid form at a temperature lower than or equal to 90° C. and higher than or equal to 70° C.

10. A process for producing polyethylene terephthalate (PET), the process comprising:

producing bis (2-hydroxyethyl) terephthalate (BHET) in liquid form by depolymerizing recycled polyethylene terephthalate (PET) by the process according to claim 1; and producing PET either by polycondensation using the BHET as a main monomer, or by polycondensation of terephthalic acid (TPA) and monoethylene glycol (MEG) using the BHET as a secondary monomer.

* * * * *